(12) United States Patent
Caneau et al.

(10) Patent No.: US 9,948,063 B2
(45) Date of Patent: Apr. 17, 2018

(54) WAVEGUIDE STRUCTURE FOR MID-IR MULTIWAVELENGTH CONCATENATED DISTRIBUTED-FEEDBACK LASER WITH AN ACTIVE CORE MADE OF CASCADED STAGES

(71) Applicant: Thorlabs Quantum Electronics, Inc., Jessup, MD (US)

(72) Inventors: Catherine Genevieve Caneau, Corning, NY (US); Feng Xie, Painted Post, NY (US); Chung-En Zah, Holmdel, NJ (US)

(73) Assignee: Thorlabs Quantum Electronics, Inc., Jessup, MD (US)

( * ) Notice: Subject to any disclaimer, the term of this patent is extended or adjusted under 35 U.S.C. 154(b) by 0 days.

(21) Appl. No.: 15/355,478

(22) Filed: Nov. 18, 2016

(65) Prior Publication Data

US 2017/0070032 A1 Mar. 9, 2017

Related U.S. Application Data

(62) Division of application No. 13/799,592, filed on Mar. 13, 2013, now Pat. No. 9,547,124.

(51) Int. Cl.
*H01S 5/20* (2006.01)
*G02B 6/10* (2006.01)
*G01N 21/17* (2006.01)
*H01S 5/0625* (2006.01)
*H01S 5/10* (2006.01)
(Continued)

(52) U.S. Cl.
CPC ........... *H01S 5/20* (2013.01); *B82Y 20/00* (2013.01); *G01N 21/17* (2013.01); *G02B 6/102* (2013.01); *H01S 5/06258* (2013.01); *H01S 5/1032* (2013.01); *H01S 5/1215* (2013.01); *H01S 5/3401* (2013.01); *H01S 5/3402* (2013.01); *H01S 5/34313* (2013.01);
(Continued)

(58) Field of Classification Search
CPC ..... G02B 6/102; H01S 5/1215; H01S 5/4087; H01S 5/1032; H01S 5/3402; H01S 5/06258; H01S 5/20
See application file for complete search history.

(56) References Cited

U.S. PATENT DOCUMENTS

| 6,600,847 B2 | 7/2003 | Saini et al. |
| 2005/0041280 A1* | 2/2005 | Lee .......................... H01S 5/50 359/344 |

(Continued)

FOREIGN PATENT DOCUMENTS

| JP | S57196592 A | 12/1982 |
| JP | 200534595949 A | 12/2005 |

OTHER PUBLICATIONS

Haus, H., et al, "Theory of Cascaded Quarter Wave Shifted Distributed Feedback Resonators," 28(1) IEEE J. Quantum Elec. 205-213 (1992).

(Continued)

*Primary Examiner* — Dung Nguyen
(74) *Attorney, Agent, or Firm* — Graham Curtin, P.A.

(57) ABSTRACT

Concatenated distributed feedback lasers having novel waveguides are disclosed. The waveguides allow for coupling of the laser beam between active and passive waveguide structures and improved device design and output efficiency. Methods of making along with methods of using such devices are also disclosed.

4 Claims, 8 Drawing Sheets

(51) Int. Cl.
    H01S 5/12      (2006.01)
    H01S 5/34      (2006.01)
    H01S 5/40      (2006.01)
    B82Y 20/00     (2011.01)
    H01S 5/343     (2006.01)
    H01S 5/028     (2006.01)
(52) U.S. Cl.
    CPC .......... *H01S 5/4087* (2013.01); *H01S 5/028* (2013.01); *H01S 2301/166* (2013.01)

(56) References Cited

U.S. PATENT DOCUMENTS

2009/0263074 A1    10/2009   Deng et al.
2012/0236889 A1     9/2012   Caneau et al.

OTHER PUBLICATIONS

E. Wang, S. So, F. Xie, C. Caneau, C. Zah and G. Wysocki, "Compact Quantum Cascade Laser Based Atmospheric CO2 Sensor," JMC5, CLEO'2011.

M. Brandstetter, A. Genner, K. Anic and B. Lendl, "Tunable external cavity quantum cascade laser for the simultaneous determination of glucose and lactate in aqueous phase," The Royal Society of Chemistry, 2010.

Illek, S., "Codirectionally Coupled Twin-Guide Laser Diode Broadband Electronic Wavelength Tuning," Electronics Letters, IEE Stevenage, GB, vol. 27, No. 24, Nov. 21, 1991.

Straub, A., "Simultaneously at Two Wavelengths (5.0 and 7.5 [micro]m) Singlemode and Tunable Quantum Cascade Distributed Feedback Lasers," Electronics Letters, IEE Stevenage, GB, vol. 38, No. 12, Jun. 6, 2002.

Namjou, K., "Sensitive Absorption Spectroscopy with a Room-Temperature Distributed-Feedback Quantum-Cascade Laser," Optics Letters, The Optical Society, vol. 23, No. 3 Feb. 1, 1998.

International Search Report with Written Opinion, dated Sep. 25, 2013, for corresponding international application PCT/US2013/032944.

Chinese First Office Action and Full English translation, along with Search Report, issued by the State Intellectual Property Office of the P.R.C. (SIPO) dated Aug. 2, 2016 for corresponding China application No. 201380015272.2.

Chinese Second Office Action and Full English translation, issued by the State Intellectual Property Office of the P.R.C. (SIPO) dated Feb. 28, 2017 for corresponding China application No. 201380015272.2.

Chinese Third Office Action and Full English translation, issued by the State Intellectual Property Office of the P.R.C. (SIPO) dated Sep. 20, 2017 for corresponding China application No. 201380015272.2.

USPTO Restriction Requirement Office Action, dated Feb. 26, 2015, for corresponding U.S. Appl. No. 13/799,592.

USPTO Non-Final Office Action dated May 25, 2016, for corresponding U.S. Appl. No. 13/799,592.

European First Office Action issued by the European Patent Office dated Feb. 2, 2018 for corresponding European application No. 13713701.4.

\* cited by examiner

WAVEGUIDE STRUCTURE FOR MID-IR MULTIWAVELENGTH CONCATENATED DISTRIBUTED-FEEDBACK LASER WITH AN ACTIVE CORE MADE OF CASCADED STAGES

CROSS REFERENCE TO RELATED APPLICATIONS

This application is a divisional of U.S. Non-provisional application Ser. No. 13/799,592 filed on Mar. 13, 2013, which claims the benefit of priority under 35 U.S.C. § 119 of U.S. Provisional Application Ser. No. 61/612,440 filed on Mar. 19, 2012. The contents of U.S. Non-provisional application Ser. No. 13/799,592 and U.S. Non-provisional application Ser. No. 13/799,592 are incorporated herein by reference.

FIELD

The present specification generally relates to semiconductor-based lasers and, more specifically, to distributed feedback lasers in the mid-infrared region that have an active core made of cascaded sections that further comprise modified waveguides to allow for improved performance. Methods of making and using such devices are also disclosed.

TECHNICAL BACKGROUND

Distributed feedback ("DFB") lasers are a solid state diode laser technology that incorporates a diffraction grating into the active region of the laser. The DFB design allows for the emission of stable, single wavelengths that are slightly tunable via temperature change. The combination of multiple DFB lasers into a concatenated DFB quantum cascade laser allows for an expansion of the tunability of this technology. However, concatenated DFB QCLs suffer from high losses when unused laser sections are unbiased, and from high power usage when biasing is used. It would be advantageous if DFB-QCLs could be created that are more power efficient and yet still offer the expanded range of wavelengths observed with concatenated DFB-QCLs.

SUMMARY

One embodiment comprises a waveguide structure comprising an active semiconductor optical waveguide made of an optical gain material; a bridge; and a passive optical waveguide; wherein the bridge is spatially located between the active waveguide and passive waveguide and wherein the active waveguide, bridge, and passive waveguide are not physically connected via an optical waveguide material. In some embodiments, the bridge comprises a periodic structure that selectively allows certain wavelengths to couple to the passive optical waveguide. In some embodiments, the active waveguide, bridge, and passive waveguide comprise GaInAs or GaAlInAs. In some embodiments, the active waveguide and bridge are parallel and from about 1 µm to about 8 µm apart at the nearest point. In some embodiments, the bridge and the passive waveguide are parallel and from about 1 µm to about 8 µm apart at the nearest point. In some embodiments, the active waveguide and bridge are parallel and from about 2 µm to about 6 µm apart at the nearest point and the bridge and the passive waveguide are parallel and from about 1 µm to about 8 µm apart at the nearest point.

Another embodiment comprises a laser comprising a gain material comprising at least two, compositionally non-identical, layers forming a superlattice, wherein the gain material generates photons by intersubband or interband transitions; at least two lasing sections placed in series, wherein each lasing section comprises gratings have non-equivalent periods or Bragg wavelengths, and wherein the lasing sections are separated by a electrical isolation region, and a waveguide structure comprising an active waveguide in contact with a gain material; at least one bridge; and a passive waveguide, wherein each bridge is spatially located between the active waveguide and passive waveguide and the active waveguide, bridge, and passive waveguide are not physically connected via a waveguide material. In some embodiments, the grating comprises phase-shifted gratings. In some embodiments, the bridge is parallel to the active waveguide and spatially centered where the light intensity is the highest. In some embodiments, the active waveguide and bridge are parallel and from about 1 µm to about 8 µm apart at the nearest point. In some embodiments, the bridge and the passive waveguide are parallel and from about 1 µm to about 8 µm apart at the nearest point. In some embodiments, the active waveguide and bridge are parallel and from about 2 µm to about 6 µm apart at the nearest point and the bridge and the passive waveguide are parallel and from about 1 µm to about 8 µm apart at the nearest point. In some embodiments, the active waveguide, bridge and passive waveguide comprise GaInAs or GaAlInAs.

In some embodiments of the laser above, the lasing sections are separated by an electric isolation region comprising a p-type layer in an n-cladding layer or by removal of the high doping part of the n-cladding layer. In some embodiments, the emission wavelength from at least one of the laser sections is from about 2.5 µm to about 15 µm. In some embodiments, at least one layer of the superlattice comprises $Ga_xIn_{1-x}As$, where x is from 0 to 1. In some embodiments, at least one layer of the superlattice comprises $Al_yIn_{1-y}As$, where y is from 0 to 1. In some embodiments, the active region comprises at least two stacks wherein the stacks with laser sections at the shortest wavelengths are placed in the center of the device. In some embodiments, the laser sections lase in pulsed mode. In some embodiments, the laser pulse width is from about 10 ns to about 1 ms. In other embodiments, the laser sections lase in continuous mode. In some embodiments, all laser sections may fire simultaneously. In other embodiments, the laser sections are fired sequentially.

Another embodiment comprises a method of detecting the signal output from a sample comprising applying at least one laser event from the laser according to one embodiment to the sample and collecting at least some of the light after it has interacted with the sample. In some embodiments, the laser wavelength is in the infrared region. In some embodiments, the collecting of the light provides information on infrared absorbance of the sample. In some embodiments, the sample is in the gas phase. In other embodiments, the sample is in the liquid phase. In still other embodiments, the sample is in the solid phase. In some embodiments, the collecting of the light provides information on infrared reflectance of the sample.

BRIEF DESCRIPTION OF DRAWINGS

FIG. 6. A longitudinal cross-section of a QCL structure with a passive waveguide below the QC core (FIG. 6A) and a front view (looking into the facet) of the same waveguide structure (FIG. 6B).

FIG. 7. Near field pattern (FIG. 7A) and the far field pattern (FIG. 7B) of a QCL structure as shown in FIG. 6, indicating that the light is propagating into the GaInAs passive waveguide layer, but is in a higher order mode.

FIG. 9. The longitudinal cross-section (FIG. 9A) and the lateral cross section (FIG. 9B) of the proposed waveguide structure with the multi-wavelength concatenated DFB QCL structure. The short GaInAs layers serve as bridges to guide the light into the passive waveguide layer beneath.

FIG. 11. The top view of an alternative structure (FIG. 11A). The passive InGaAs waveguide structure, and the bridge InGaAs structures are located on the side of the laser ridge.

DETAILED DESCRIPTION

The present description can be understood more readily by reference to the following embodiments, drawings, examples, and claims, and their previous and following description. However, before the present compositions, articles, devices, and methods are disclosed and described, it is to be understood that this description is not limited to the specific compositions, articles, devices, and methods disclosed unless otherwise specified, as such can, of course, vary. It is also to be understood that the terminology used herein is for the purpose of describing particular aspects only and is not intended to be limiting.

The following description is provided as an enabling teaching in its currently known embodiments. To this end, those skilled in the relevant art will recognize and appreciate that many changes can be made to the various aspects described herein, while still obtaining the beneficial results. It will also be apparent that some of the desired benefits can be obtained by selecting some of the features without utilizing other features. Accordingly, those who work in the art will recognize that many modifications and adaptations are possible and can even be desirable in certain circumstances. Thus, the following description is provided as illustrative and not in limitation thereof.

Disclosed are materials, compounds, compositions, and components that can be used for, can be used in conjunction with, can be used in preparation for, or are embodiments of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of substituents A, B, and C are disclosed as well as a class of substituents D, E, and F, and an example of a combination embodiment, A-D is disclosed, then each is individually and collectively contemplated. Thus, in this example, each of the combinations A-E, A-F, B-D, B-E, B-F, C-D, C-E, and C-F are specifically contemplated and should be considered disclosed from disclosure of A, B, and/or C; D, E, and/or F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and/or C; D, E, and/or F; and the example combination A-D. This concept applies to all aspects of this disclosure including, but not limited to any components of the compositions and steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In this specification and in the claims which follow, reference will be made to a number of terms which shall be defined to have the following meanings:

"Include," "includes," or like terms means encompassing but not limited to, that is, inclusive and not exclusive.

The term "about" references all terms in the range unless otherwise stated. For example, about 1, 2, or 3 is equivalent to about 1, about 2, or about 3, and further comprises from about 1-3, from about 1-2, and from about 2-3. Specific and preferred values disclosed for compositions, components, ingredients, additives, and like aspects, and ranges thereof, are for illustration only; they do not exclude other defined values or other values within defined ranges. The compositions and methods of the disclosure include those having any value or any combination of the values, specific values, more specific values, and preferred values described herein.

The indefinite article "a" or "an" and its corresponding definite article "the" as used herein means at least one, or one or more, unless specified otherwise.

As used herein, a "superlattice" comprises at least two semiconductor materials with different bandgaps that produce quantum well confinement and intersubband transition (see, e.g., U.S. Appl. No. 61/564,375, herein incorporated by reference in its entirety). The thicknesses of the at least two semiconductor materials may change within lattice or may be of constant thickness. If the thicknesses of the materials change, they may change in a linear or nonlinear fashion.

As used herein, a "stage" comprises a series of quantum wells formed by the superlattice that allow electrons to transition from an injector region to an active region. As used herein, a "stack" comprises a series of stages. The "active region" or "core" is comprised of at least one stack and is used to describe the region of the laser that produces the light emission.

As used herein an "optical waveguide" comprises a dielectric material with a high refractive or dielectric index surrounded by one or more dielectric materials with a low refractive or dielectric index, wherein the indices are measured at the wavelengths of interest. As used herein, a "waveguide material" comprises a dielectric material with a high refractive index at the wavelengths of interest.

Figure 3:
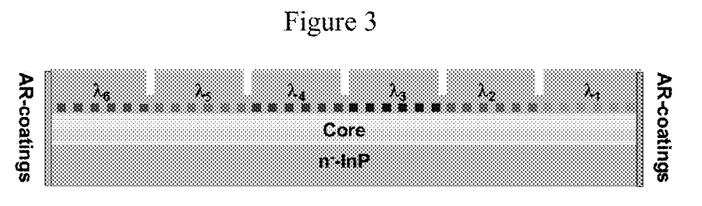
FIG. 3. An embodiment comprising a mid-IR multiwavelength concatenated DFB QCL with an active core made of cascaded stages.
Figure 4:
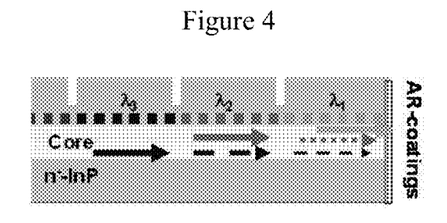
FIG. 4. The embodiment in FIG. 3, wherein the light emitted in the second or the third DFB section will experience high loss at the unbiased core section of the DFB sections in front of it.

A concatenated DFB QCL structure allows multiple wavelengths (single mode) to be emitted from one single facet, as shown in FIG. 3 and described in U.S. Appl. No. 61/586,327, hereby incorporated by reference in its entirety. The first DFB section lases at $\lambda_1$, the second DFB section lases at $\lambda_2$, etc. However, the light emitted by the second section or any but the first DFB section, will have to propagate through the DFB sections in front of it, as shown in FIG. 4. If those sections in front are not biased, the loss in those unbiased regions can be high (>20 cm$^{-1}$). The loss mostly results from the passage of $\lambda_2$ (or $\lambda_3$, $\lambda_4$, $\lambda_5$, etc.) through the unbiased core region. For example, the light intensity of $\lambda_2$ is much lower than that of $\lambda_1$, even though the gain/core section of two DFB sections are shared, and the difference between $\lambda_1$ and $\lambda_2$ is small.

Figure 5:
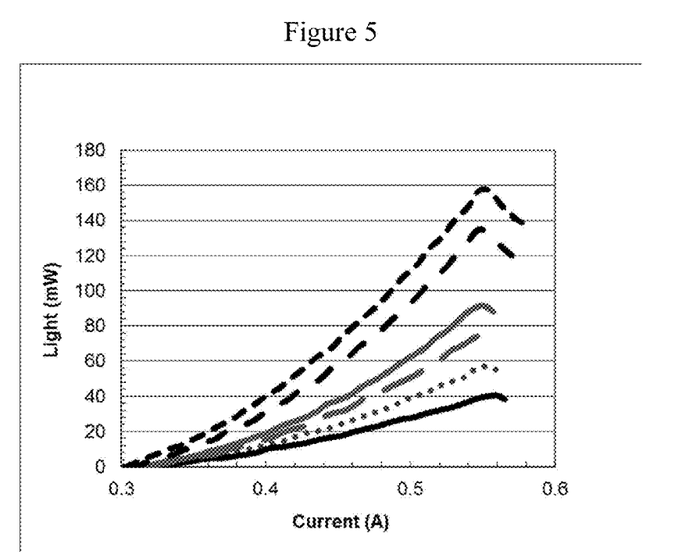
FIG. 5. Pulsed light-current curves of the second DFB QCL as a function of DC bias in the first DFB QCL next to the front facet. The bias was 11V (black, close dash; - - - ); 10V (black, spaced dash; - - - ); 9V (grey solid; - - - ); 8V (grey, long spaced dash; - - - ); 4V (grey dot; . . . ); and 0V (black solid; - - - ).

One can reduce the loss in section one when operating section two, by biasing the section one at the same time (below threshold voltage). The intensity of $\lambda_2$ will increase, as shown in FIG. 5. The bias was 11V(black, close dash; - - - ); 10V (black, spaced dash; - - -); 9V (grey solid; . . . ); 8V (grey, long spaced dash, - - - ); 4V (grey dot; . . . ); and 0V (black solid; - - - ). As is shown, there is a four-fold increase in power going from a bias of 0V to 11V. However, there is a commensurate increase in the total power consumption, and therefore reduce wall plug efficiency (WPE).

In order to avoid the losses associated with propagation through unbiased sections, it is possible to guide the light (e.g., $\lambda_2$, $\lambda_3$, $\lambda_4$, $\lambda_5$, etc.) out of the device through an additional waveguide and avoid the unbiased core of the sections in the front.

A first embodiment comprises a waveguide structure that passively guides light out of the gain region and into an adjacent waveguide layer. In some embodiments, the adjacent optical waveguides may comprise one or more layers of suitable material that are electromagnetically coupled, but not physically linked, to the gain section. Embodiments of this waveguide structure may decrease loss of intensity as light would pass through the adjacent waveguide rather than through the core of the sections in the front. In some embodiments, the waveguide structure allows for non-emitting DFB sections to be maintained in an unbiased state and not affect the laser output.

Another embodiment comprises a concatenated DFB laser further comprising a waveguide structure that passively guides light out of the gain region and into an adjacent waveguide layer. In some embodiments, the waveguide structure comprises one or more adjacent optical waveguides, wherein the adjacent optical waveguides may comprise one or more layers of suitable material that are electromagnetically coupled, but not physically linked, to the gain section. The multi-wavelength concatenated DFB ("cDFB") laser may comprise an active core made of a series of cascaded sections to generate multiple wavelengths simultaneously or sequentially in time. In some embodiments, the cDFB laser lases in the infrared ("IR") region. In some embodiments, the cDFB lases in the region from about 2.5 µm to about 15 µm. Such a device is capable of sampling a broad absorption line of a single molecule or several absorption lines from different molecules. Methods of forming embodiments may comprise using a fabrication process similar to that used in distributed feedback ("DFB") quantum cascade lasers ("QCLs"). Embodiments herein are advantageous in that they can replace wavelength tunable external cavity ("EC") QCLs due to smaller sizes, faster speeds and lower costs. Further, embodiments also have size and cost advantages over a DFB QCL arrays because DFB QCL arrays need optical combining optics to combine the output of an array into one optical beam.

Figure 1:
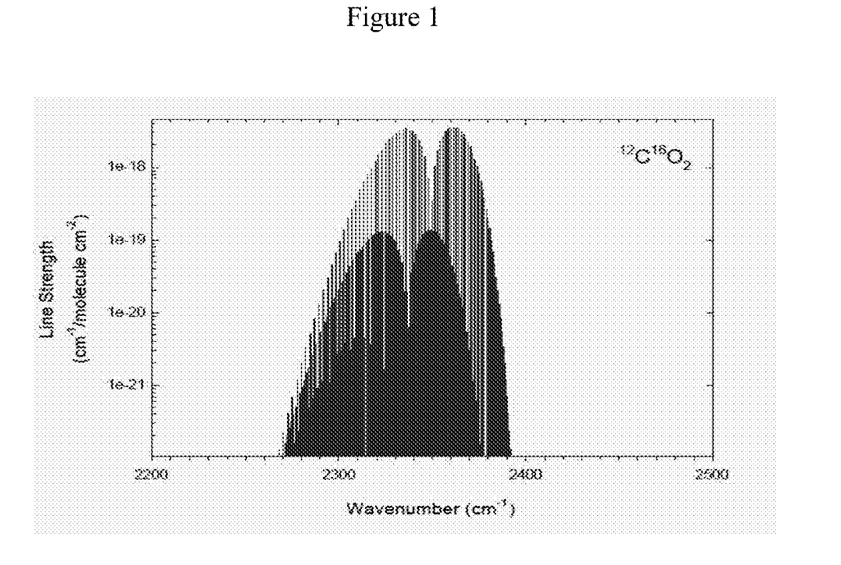
FIG. 1. Absorption spectrum of $CO_2$ near 2350 $cm^{-1}$.
Figure 2:
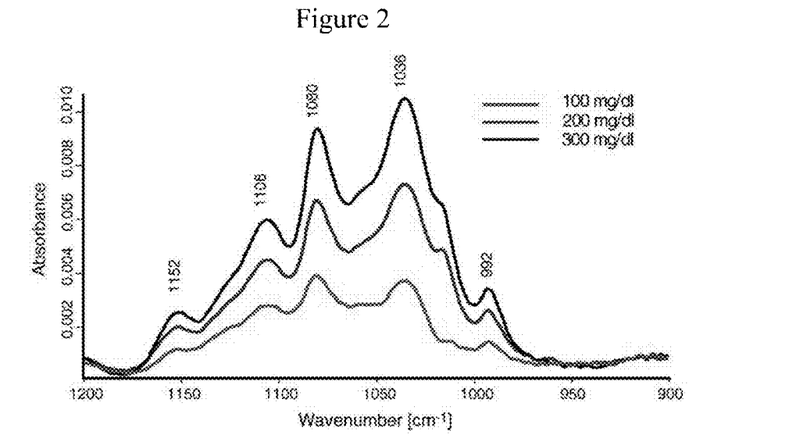
FIG. 2. Absorption spectrum of glucose.

One particular application where embodiments may be useful is in chemical analysis via infrared ("IR") spectroscopy. The strong absorption lines in the mid-IR region from the vibration of chemical bonds can be used to identify molecular composition. Mid-IR wavelength tunable sources like DFB QCLs may be used to scan the wavelength around an absorption line. While traditional DFB QCLs have a small wavelength tuning range of about 10 cm$^{-1}$ and are often used to detect one of narrow absorption lines, such as that of a small molecule (as an example, FIG. 1 shows the absorption lines of $CO_2$ near 2350 cm$^{-1}$, i.e. around 4.2-4.3 µm), embodiments may have much larger wavelength coverage and may be used to detect the broad absorption line of a large molecule (FIG. 2 shows the absorption at 950-1200 cm$^{-1}$ of glucose).

Figure 6A:
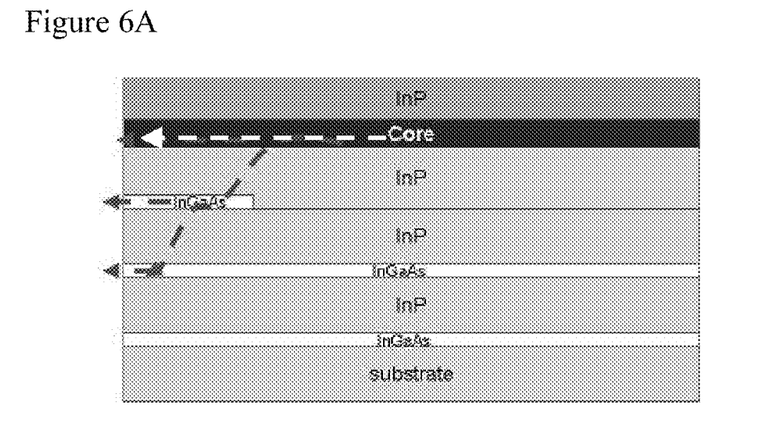
Figure 6B:
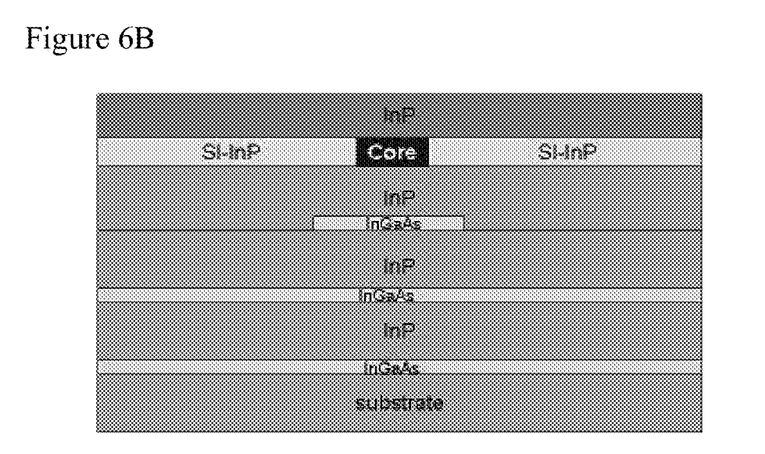

The core provides the optical gain needed to achieve lasing. The core of the laser may comprise a stack of quantum cascade ("QC") or interband cascade ("IC") regions. Any QC or IC structure with broad optical gain may be used. In some embodiments, the core comprises a QC structure. In some embodiments, the core comprises an IC structure. The gain peak of each core is designed to be near one of the sampling wavelengths, as shown in FIG. 6. The cores with optical gain at shorter wavelength normally should be placed closer to the center of the optical mode since the optical mode of shorter wavelength is narrower than that of longer wavelength.

Embodiments may comprise a gain material comprising at least two, compositionally non-identical, layers forming a superlattice. By proper design of the layer thicknesses, it is possible to engineer a population inversion between two subbands in the system which is necessary to achieve laser emission. The thickness of the layers may be identical or may be different depending on the desired design. In some embodiments, the layers have a thickness from about 1 Å to about 500 Å. In some embodiments, the layers have a thickness from about 10 Å to about 100 Å. In some embodiments, the layers have a thickness of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200, 250, 300, 350, 400, 450, or 500 Å.

Materials that may be used to form the layers in the gain material generally comprise semiconductors, such as group IV, III-V, and II-VI semiconductors. In some embodiments, the layers may comprise GaAs, GaSb, InAs, $Al_xGa_{1-x}As$, $Si_xGe_{1-x}$, or $Ga_xIn_{1-x}As$, $Al_yIn_{1-y}As$, $G_xaIn_{1-x}Sb$, and $Al_xIn_{1-x}Sb$ wherein x and y are from 0 to 1.

The superlattice gain material may be produced using various techniques, for example molecular-beam epitaxy (MBE) (including gas-source MBE and MO-MBE), metal organic vapor phase epitaxy (MOVPE), or sputtering. These methods allow production of layers with thicknesses of only a few atomic spacings.

Figure 9A:
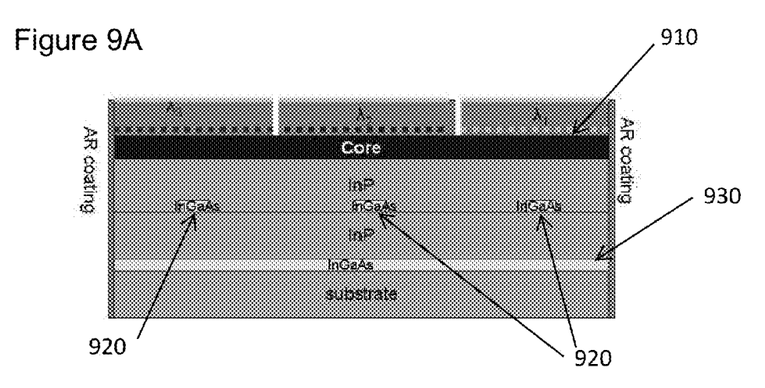
Figure 9B:
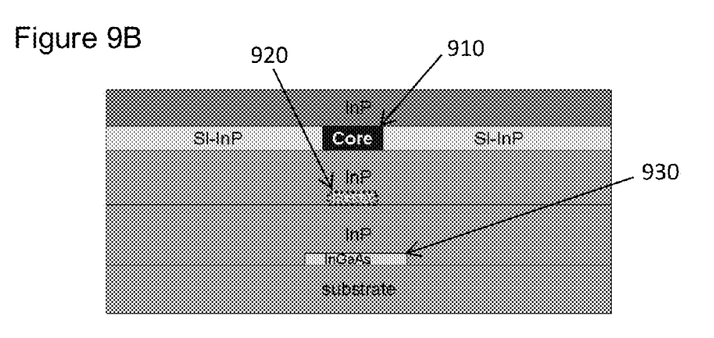

Embodiments further comprise an optical waveguide. An optical waveguide, as used herein, comprises a physical structure that guides electromagnetic waves in the optical spectrum. Embodiments comprise an optical waveguide that allows unused sections to be maintained in an unbiased state and not affect laser output. Optical waveguides embodied herein may comprise multiple layers of suitable material that are electromagnetically coupled, but not physically linked, for example as shown in FIG. 9. In some embodiments, the active waveguide layer comprises a ridge waveguide, which is created by etching parallel trenches in the quantum cascade gain material to create an isolated stripe of QC material.

Optical waveguides embodied herein may comprise a bridge layer ('bridge"). The bridge comprises a short section of waveguide suitable material, such as GaInAs. The bridge may be located in the center of each DFB section if the DFB sections are quarter wave shifted. Alternatively, the bridge may be located where the light intensity is longitudinally maximized. In some embodiments, the bridge may comprise a grating layer. In such embodiments, the bridge may selectively wavelength couple two waveguides with different effective refractive indices.

Figure 10:
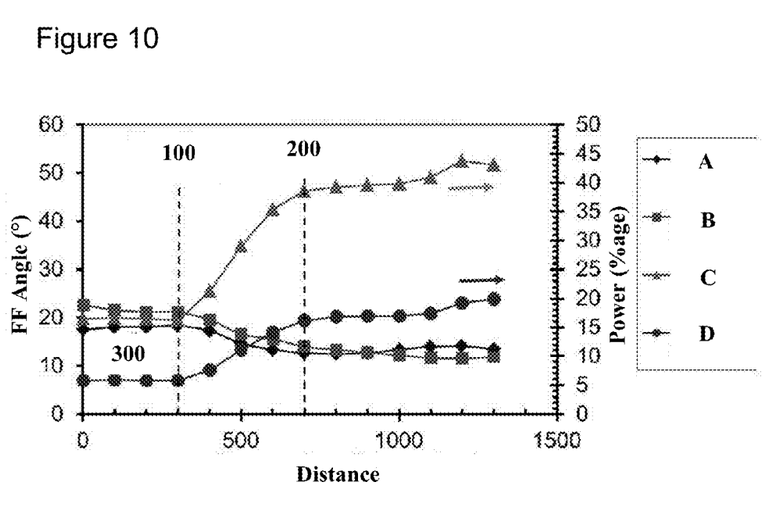
FIG. 10. A diagram showing a comparative simulation of the FF angle and power (percentage) within the 10 and 5 degrees solid angle for the QCL waveguide structure shown in FIG. 6. The waveguide structure is a triple GaInAs-layer structure (0.67 µm, 0.65 µm, 0.65 µm) with an interval of d=3.5 µm. The short GaInAs insert started at position 300 µm. The FF angle decreasing and the light intensity within the 10 and 5 degrees angle increasing indicates that the light propagates into the passive waveguide layers. It takes about 300-400 µm to stabilize. It is simulated with $\lambda=4.6$ µm.

The index, width, and length of the bridge interacting with each DFB section for wavelength $\lambda_i$ may be determined in such a way that the light with wavelength $\lambda_i$ can propagate into a passive waveguide layer. The index may be changed by doping density or composition (adding a small amount of AlInAs). The bridge should be longer than a certain value to ensure that the beam propagates into the passive waveguide beneath. For example it should be about 300~400 μm long for the waveguide structure of $\lambda$~4.6 μm, as shown in FIG. 10. FIG. 10 shows a comparative simulation of the FF angle and power (percentage) within the 10 and 5 degrees solid angle for the QCL waveguide structure shown in FIG. 6 with $\lambda$=4.6 μm. The waveguide structure is a triple GaInAs-layer structure (0.67 μm, 0.65 μm, 0.65 μm) with an interval of d=3.5 μm. Region 300 is a grading period. The short GaInAs insert starts at position 100, approximately 300 μm in, and ends at 200. The vertical far field ("A") and horizontal far field ("B") angles of the beam reflect the optical mode size before exiting the waveguide and decrease upon interaction with the insert. The percentage power within 10° solid angle ("C") and 5° solid angle ("D") show significant increases that steadily grow upon interaction with the insert. The FF angle decreasing and the light intensity within the 10 and 5 degrees angle increasing indicates that the light propagates into the passive waveguide layers and that it takes about 300-400 μm to stabilize.

In some embodiments, the bridge is about 100, 150, 200, 250, 300, 350, 400, 450, 500, 550, 600, 650, 700, 800, 900, 1000, 1100, 1200, 1300, 1400, 1500, 1600, 1700, 1800, 1900, or 2000 μm in length. The distance between the bridge and upper waveguide (and between the bridge and lower waveguide) may be determined in such a way that the optical mode in the upper waveguide (or lower waveguide) has a small (or finite) but none zero overlap with the optical mode in the bridge structure. The mode in the upper waveguide may then transit (or merge) into the bridge structure and further into the lower waveguide layer effectively. The distance is a function of wavelength, and also the waveguide structure (thickness and refractive index of each layer). In the case of the waveguide structure for $\lambda$~4.6 μm, the distance comprises about 3.5 μm, while the thickness of the bridge (and lower waveguide layer) of GaInAs comprises about 0.65 μm. In some embodiments, the distance between the bridge and upper waveguide comprises about 0.5, 0.75, 1.0, 1.25, 1.5, 1.75, 2.0, 2.25, 2.5, 2.75, 3.0, 3.25, 3.5, 3.75, 4.0, 4.25, 4.5, 4.74, 5.0, 5.25, 5.5, 5.75, or 6.0 μm. In some embodiments, the distance between the bridge and passive (lower) waveguide comprises about 0.5, 0.75, 1.0, 1.25, 1.5, 1.75, 2.0, 2.25, 2.5, 2.75, 3.0, 3.25, 3.5, 3.75, 4.0, 4.25, 4.5, 4.74, 5.0, 5.25, 5.5, 5.75, or 6.0 μm.

Optical waveguides embodied herein may comprise a passive waveguide layer. The passive waveguide layer may comprise a suitable material that allows for laser propagation at the desired wavelength, such as GaInAs. The passive waveguide may comprise the dimensions from about 1 μm to about 20 μm in width and up to several mm in length (the length is usually defined by cleaving). In some embodiments, the passive waveguide is about 1, 2, 3, 4, 5, 6, 7, 8, 9, 10, 11, 12, 13, 14, 15, 16, 17, 18, 19, or 20 μm in width and about 100, 150, 200, 250, 300, 400, 500, 600, 700, 800, 900, 1000, 1500, 2000, 3000, 4000, 5000, 6000, 7000, 8000, 9000, or 10,000 μm in length. In some embodiments, the thickness of the bridge and passive waveguide are each independently about 0.05, 0.1, 0.2, 0.3, 0.4, 0.45, 0.5, 0.55, 0.6, 0.65, 0.7, 0.75, 0.8, 0.9, 1.0, 1.1, 1.2, 1.3, 1.4, 1.5, 1.6, 1.7, 1.8, 1.9, or 2.0 μm. Lateral mode confinement may be achieved by the deposition in the trenches of a dielectric material, and then the entire ridge may be coated with gold to help remove heat from the ridge when it is producing light. More commonly, lateral mode confinement is achieved by growing in the trenches a semi-insulating material such as InP if the laser was grown on InP substrate. Light may be emitted from the cleaved ends of the passive waveguide.

The bridge and passive waveguide layers may be constructed to be parallel to the active waveguide and/or to each other. As used herein, "parallel" means that the planes formed by the length and width of the structures are approximately equidistant everywhere and/or have the same angle relative to a common plane. In some embodiments, parallel means that the planes have the same angle ±5, ±4, ±3, ±2, or 1±°.

Moreover, with this design, the DFB sections with longer wavelengths should be located in the front part of the whole structure, and the DFB sections with shorter wavelengths should be located in the back. The light of shorter wavelength will propagate through the passive waveguide layer without leaking into the front DFB sections with longer wavelength, because the mode overlap to the "bridge" GaInAs layer is smaller for shorter wavelength.

Embodiments may further comprise an antireflection or antireflective (AR) layer. As used herein an AR layer comprises an optical coating applied to at least one end (facet) of the device and that reduces reflection, particularly in the IR region. The AR layers may be of any type, such as index-matching, single layer interference, multi-layer interference, or moth eye (nanostructured). In some embodiments, the AR coatings provide less than about 10%, 5%, 4%, 3%, 2%, 1%, 0.5%, 0.1%, 0.01%, 0.001%, or 0% loss.

Embodiments further comprise at least two laser sections placed in series, each laser section comprising a phase shifted grating, wherein the gratings have non-equivalent periods or Bragg wavelength. A grating, as used herein comprises a structure formed from multiple layers of alternating materials with varying refractive index, or by periodic variation of some characteristic (such as height), resulting in periodic variation in the effective refractive index in the guide. Each layer boundary causes a partial reflection of an optical wave. For waves propagating through the mth order grating, whose wavelength is close to $$\frac{2}{m}$$

times the multiplication of the period and the effective refractive index, the many reflections combine with constructive interference, and the grating acts as a high-quality reflector. Phase shifted gratings may comprise, for example, ⅛, ¼, or other phase shifted gratings.

The use of quarter-wave shifted, distributed feedback resonators in diode lasers is advantageous as they provide a resonance at the center of the grating stopband that is of higher quality factor than the resonances to either side. The narrowband resonance of a quarter wave shifted DFB transmission resonator has a Lorentzian response. Further information on the use of quarter wave shifted resonators can be found in H. Haus and Y. Lai, *Theory of Cascaded Quarter Wave Shifted Distributed Feedback Resonators*, 28(1) IEEE J. QUANTUM ELEC. 205-213 (1992), herein incorporated by reference in its entirety.

Gratings with multiple periods can be patterned by electron beam ("e-beam") writing or contact printing of a grating mask manufactured by e-beam lithography.

Additional components that may be found in embodiments comprise n-type cladding layers both above and/or below the gain material. The active gain and wavelength selective sections may be capped with a patterned electrical contact layer which comprises respective control electrodes dedicated to the different laser sections. An insulating dielectric material may be deposited in appropriate regions in the patterned electrical contact layer to isolate electrically the distinct regions of the laser structure.

In some embodiments, the lasing sections are separated by a p-type electrical isolation region, as described in U.S. application Ser. No. 13/050,026, incorporated by reference herein in its entirety. For example, an active waveguide core may be sandwiched between upper and lower n-type cladding layers. The active core and the lower n-type cladding layer, as well as at least part of the upper cladding layer, extend through the electrically isolated laser sections of the embodiment. A portion or portions of the upper n-type cladding layer comprise sufficient p-type dopant to define p-type electrical isolation region(s), which extend across part of the thickness of the upper n-type cladding layer along a projection separating the sections of the embodiment. The upper and lower n-type cladding layers may comprise InP, GaAs, AlGaAs, or any other conventional or yet-to-be developed cladding material suitable. For example, and not by way of limitation, it is contemplated that a variety of cladding materials might be suitable, including II-VI semiconductors, Si—Ge or GaN-based materials, etc. Additional methods of separating the lasing sections are described in U.S. Appl. No. 61/586,327, incorporated by reference herein in its entirety.

By way of example, and not limitation, it is alternatively contemplated that the upper and lower n-type cladding layers may be GaAs-based cladding layers. Some of the cladding layers may be AlGaAs or (Al)GaInP instead of simply GaAs. For GaAs-based cladding layers, the core may be GaAs/AlGaAs, AlGaAs/AlGaAs, (Al)GaInP/(Al)GaInP, or GaInAs/(Al)GaAs. Additional layers of similar composition are contemplated for the remaining layers of the structure and should be selected to compensate for any lattice-mismatch between GaInAs and the GaAs substrate. For example, and not by way of limitation, other possible layers are GaInP, AlGaInP, GaAsP, and GaInAsP. For GaAs-based cladding layers, suitable dopants used to make (Al) GaAs semi-insulating include, but are not limited to Cr and O. At very low temperature growth, semi-insulating (Al) GaAs can be obtained without any dopant.

Embodiments herein may be used in either a pulsed or continuous-wave mode. Laser pulse duration may be from about 1 ns to about 1 ms. In some embodiments, the pulse width at FWHM is about 1 ns, 2 ns, 3 ns, 4 ns, 5 ns, 6 ns, 7 ns, 8 ns, 9 ns, 10 ns, 20 ns, 50 ns, 60 ns, 70 ns, 80 ns, 90 ns, 100 ns, 200 ns, 300 ns, 400 ns, 500 ns, 600 ns, 700 ns, 800 ns, 900 ns, 1 µs, 10 µs, 100 µs, or 1 ms. In some embodiments, devices embodied herein may be designed to fire all laser sections simultaneously, individually, and/or in a sequential or programmed order.

The embodiments described herein have tunabilities over 100 cm$^{-1}$, over 200 cm$^{-1}$, over 300 cm$^{-1}$, over 400 cm$^{-1}$, or over 500 cm$^{-1}$. In some embodiments, the cDFBs embodiments have wavelength span from about 100 cm$^{-1}$ to about 500 cm$^{-1}$.

The peak wavelength of the laser sections may be selected to be the sampling wavelengths ($\lambda_{si}$, I=1 to n) of a broad absorption line of one molecule or several absorption lines from different molecules. In some embodiments, the cDFB lases in the region from about 2.5 µm to about 15 µm. In some embodiments, the cDFB lases at about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0 µm.

Embodiments may be used in any number of methods wherein IR radiation, and particular IR laser radiation would be advantageous. Particular applications include IR absorbance or reflectance measurements, IR and FTIR spectroscopies, Raman spectroscopy, gas and/or chemical weapons detection, chemical dynamics and kinetics measurements, thermal experiments, etc. In one embodiment, the embodiments are used in IR absorbance measurements to identify molecular compositions.

EXAMPLES

Example 1

Figure 7A:
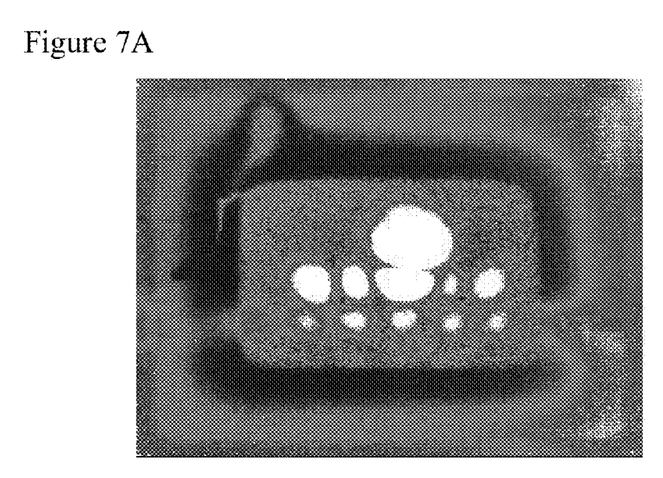
Figure 7B:
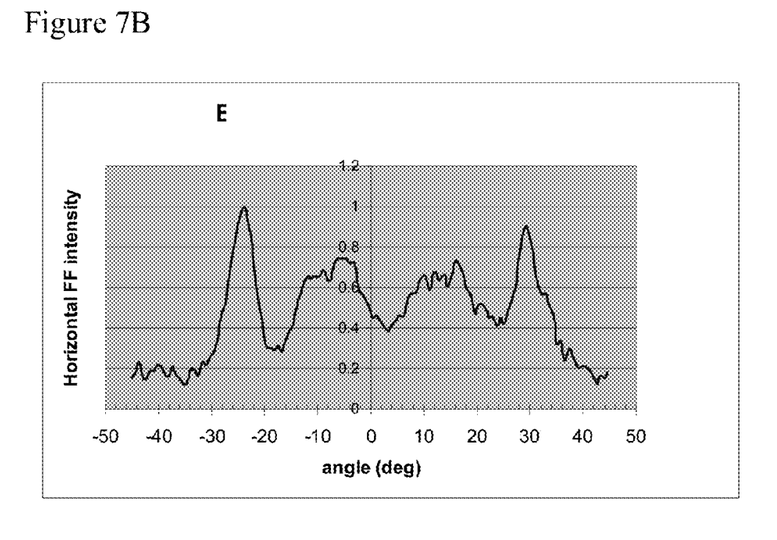
Figure 8:
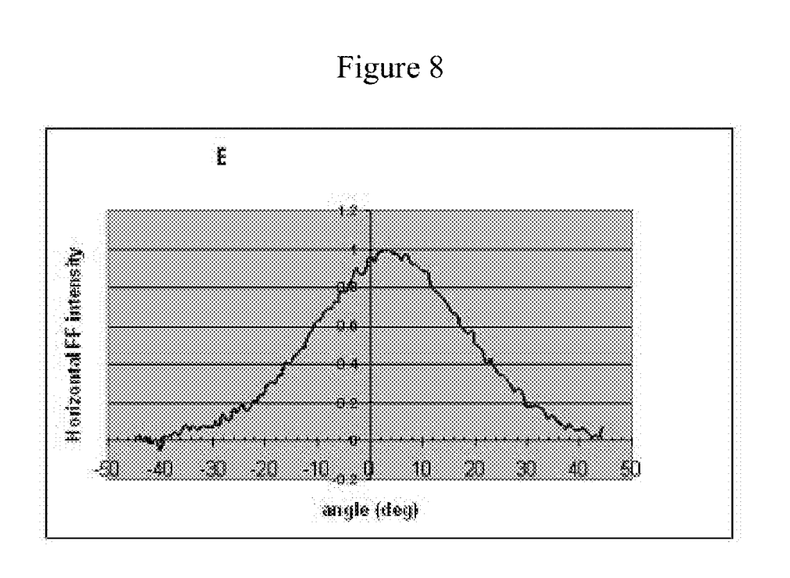
FIG. 8. The far field pattern of a QCL structure as shown in FIG. 6, but without the first short GaInAs layer. This is an example of a FF pattern with a good fundamental mode, indicating that no light is propagating into the lower GaInAs layer.

The waveguide structure in FIG. 6 was designed to demonstrate small far field angle, by guiding the light into the waveguide layers of GaInAs beneath the core layer, and expanding the optical mode. The short GaInAs layer (the first layer beneath the core) is located near the front facet, so that the light can only be guided into the waveguide layers near the front facet. The result was only partially successful. Light was guided into the waveguide structure as designed, as shown in FIG. 7, thus proving that we can guide light out at any chosen point, by placing the short first layer of GaInAs. However, due to the large width (for the purpose of small far field angle) of the waveguide layer, higher order modes were excited, instead of the fundamental mode. FIG. 8 shows that without the first layer of GaInAs, the light will not be guided into the 2nd waveguide layer as the overlap between the two optical modes is too small.

Example 2

Prospective

A proposed waveguide structure for the multiwavelength concatenated DFB QCL structure is shown in FIG. 9. The light emitted by each DFB section will be guided into the waveguide layer 910 (e.g., GaInAs) beneath each section through the bridge layer 920 (for example, comprising GaInAs). The bridge may be placed in the center of each DFB section, where the light intensity in a quarter-wave-shifted DFB structure reaches maximum. This structure comprises a single passive waveguide layer 930 going through the whole structure and the design of this layer should be narrow enough (~8 µm) to avoid higher order modes. Guiding the light through the passive waveguide will allow the light to experience much less loss because the loss of low-doped GaInAs is in the range of 1~2 cm$^{-1}$. It can be further reduced by reducing the doping in the GaInAs layers.

Example 3

Prospective

Figure 11A:
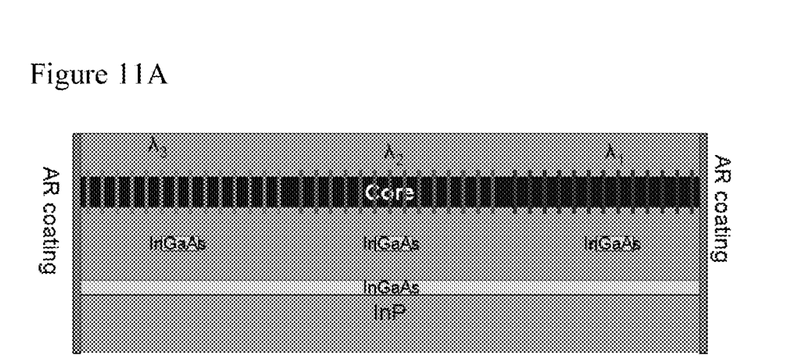
Figure 11B:
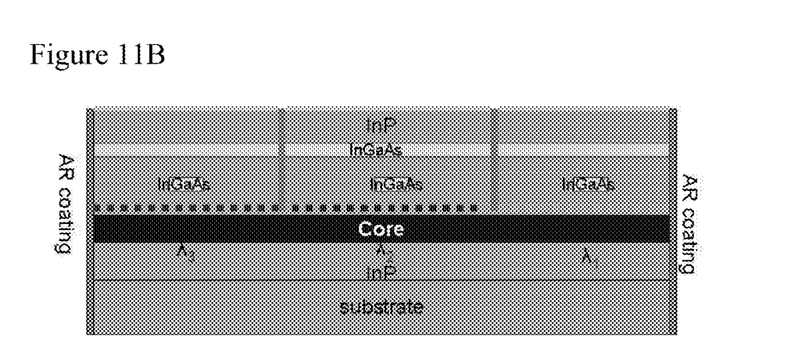
FIG. 11B shows the longitudinal cross-section of an alternative waveguide structure in combination with the multi-wavelength concatenated DFB QCL. The short GaInAs layers serve as bridges to guide the light into the passive waveguide layer above. The trenches can be replaced by semi-insolating InP (SI-InP) (Iron doped).

An alternative proposed waveguide structure for the multiwavelength concatenated DFB QCL structure is shown in FIG. 11. FIG. 11A shows the top view of the structure wherein the bridge and passive waveguide are located to the side of the laser ridge. FIG. 11B describes the longitudinal cross section of the alternative waveguide, showing that the bridge is located at a height between the passive waveguide and the active layer. The waveguide layers may comprise any number of compositions that are transmissive at the requisite wavelength.

We claim:
1. A waveguide structure comprising:
a. an active semiconductor optical waveguide made of an optical gain material;
b. a bridge; and
c. a passive optical waveguide; wherein:
the bridge is spatially located between the active semiconductor optical waveguide and the passive optical waveguide; and
the active semiconductor optical waveguide, the bridge, and the passive optical waveguide are not physically connected via an optical waveguide material;
wherein the active semiconductor optical waveguide, the bridge, and passive optical waveguide comprise GaInAs or GaAlInAs.

2. The waveguide structure of claim 1, wherein the bridge comprises a periodic structure that selectively allows certain wavelengths of light to couple to the passive optical waveguide.

3. The waveguide structure of claim 1, wherein the active semiconductor optical waveguide and the bridge, or the bridge and the passive optical waveguide are parallel and from about 1 µm to about 8 µm apart at the nearest point.

4. The waveguide structure of claim 1 wherein the active semiconductor optical waveguide and the bridge are parallel and from about 2 µm to about 6 µm apart at the nearest point and the bridge and the passive optical waveguide are parallel and from about 1 µm to about 8 µm apart at the nearest point.

* * * * *